US012623986B2

(12) United States Patent
Sumpena et al.

(10) Patent No.: US 12,623,986 B2
(45) Date of Patent: May 12, 2026

(54) SYNERGISTIC USE OF PHENOL PURIFICATION TRAIN IN PHENOL PRODUCTION UNIT FOR PROCESSING PHENOLIC WATER FROM BISPHENOL-A PRODUCTION UNIT

(71) Applicant: SABIC Global Technologies B.V., Bergen op Zoom (NL)

(72) Inventors: Kadek Sumpena, Nederweert (NL); Lara Galan-Sanchez, Eindhoven (NL); Frank Mostert, Maastricht (NL); Kae Shin Wong, Maasmechelen (BE)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 482 days.

(21) Appl. No.: 18/030,284

(22) PCT Filed: Oct. 8, 2021

(86) PCT No.: PCT/IB2021/059240
§ 371 (c)(1),
(2) Date: Apr. 5, 2023

(87) PCT Pub. No.: WO2022/074619
PCT Pub. Date: Apr. 14, 2022

(65) Prior Publication Data
US 2024/0018080 A1 Jan. 18, 2024

Related U.S. Application Data

(60) Provisional application No. 63/090,125, filed on Oct. 9, 2020.

(51) Int. Cl.
| | |
|---|---|
| *C07C 37/74* | (2006.01) |
| *C02F 1/26* | (2023.01) |
| *C07C 37/72* | (2006.01) |
| *C02F 101/34* | (2006.01) |
| *C02F 103/36* | (2006.01) |

(52) U.S. Cl.
CPC .............. *C07C 37/74* (2013.01); *C02F 1/26* (2013.01); *C07C 37/72* (2013.01); *C02F 2101/345* (2013.01); *C02F 2103/36* (2013.01)

(58) Field of Classification Search
CPC ........... C07C 37/74; C07C 37/72; C02F 1/26
See application file for complete search history.

(56) References Cited

U.S. PATENT DOCUMENTS

| | | | | |
|---|---|---|---|---|
| 4,469,561 A | * | 9/1984 | Sikdar | C02F 1/26 |
| | | | | 568/748 |
| 8,044,248 B2 | | 10/2011 | Palmer | |
| 8,088,956 B2 | | 1/2012 | Palmer | |
| 10,407,370 B2 | * | 9/2019 | Nelson | C07C 37/20 |
| 2010/0105960 A1 | | 4/2010 | Evitt et al. | |

FOREIGN PATENT DOCUMENTS

| | | |
|---|---|---|
| CN | 101715436 A | 5/2010 |
| CN | 102015598 A | 4/2011 |
| EP | 3210963 A1 | 8/2017 |
| JP | 3775832 B2 | 4/1997 |
| WO | 2017044229 A1 | 3/2017 |

OTHER PUBLICATIONS

Office Action for the corresponding Chinese Application No. 202180069148.9, Date of Issue: May 20, 2025; 9 pages (English translation).
International Search Report for International Application No. PCT/IB2021/059240; International Filing Date Oct. 8, 2021; Date of Mailing Feb. 2, 2022; 3 pages.
Written Opinion for International Application No. PCT/IB2021/059240; International Filing Date Oct. 8, 2021; Date of Mailing Feb. 2, 2022; 5 pages.
Chinese Office Action issued Nov. 29, 2024 for corresponding Chinese Application No. 202180069148.9, English translation, 8 pages.
United Arab Emirates Office Action issued Dec. 23, 2024 for corresponding UAE Application No. P6000825/2023 filed Apr. 10, 2023, English translation, 8 p. (Search Report, p. 8).

* cited by examiner

*Primary Examiner* — Sikarl A Witherspoon
(74) *Attorney, Agent, or Firm* — CANTOR COLBURN LLP

(57) ABSTRACT

Systems and methods for recovering phenol have been disclosed. At least a portion of a wastewater stream from a bisphenol-A production process and a phenol stream that is produced by separating a crude phenol stream from a cumene based phenol production process are concurrently processed in a hydrocarbon removal unit to produce (i) a purified phenol stream comprising 95 to 99.9 wt. % phenol and (ii) an aqueous stream comprising water and byproducts of the phenol production process.

15 Claims, 2 Drawing Sheets

100

16 — To neutralizer/ dephenolation

Phenolic Water from BPA Plant
15

Hydrocarbon Removal Column 102

12

Crude Phenol Column 101

Crude Phenol 11

Phenol to Finishing Column
17

13 — Heavies

22 — Spent Solvent

Phenolic Water
14      21

Dephenolation Unit
103

Recycle to Phenol Plant
18

Wastewater to Biotreatment
19

200 ⌐

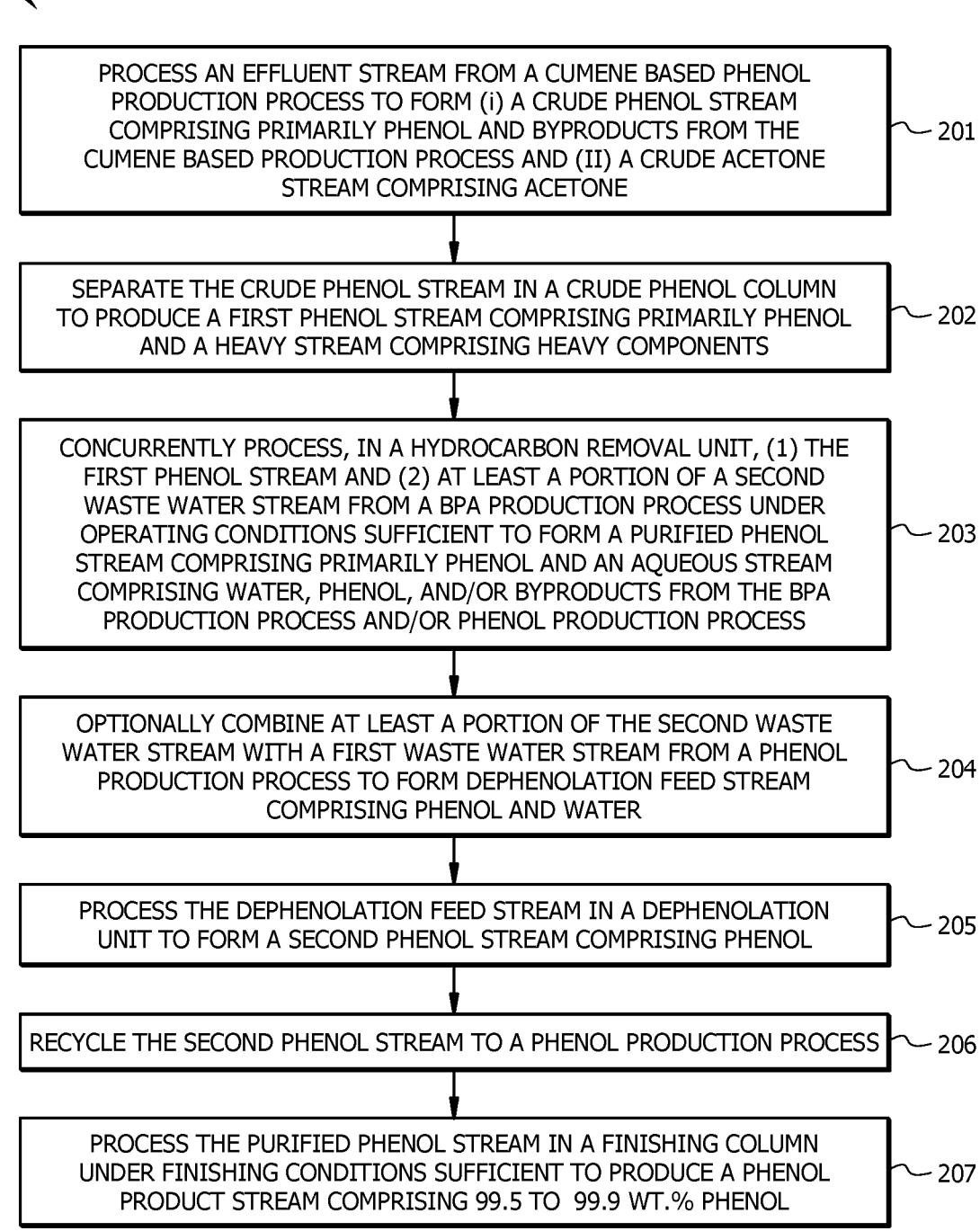

PROCESS AN EFFLUENT STREAM FROM A CUMENE BASED PHENOL PRODUCTION PROCESS TO FORM (i) A CRUDE PHENOL STREAM COMPRISING PRIMARILY PHENOL AND BYPRODUCTS FROM THE CUMENE BASED PRODUCTION PROCESS AND (II) A CRUDE ACETONE STREAM COMPRISING ACETONE — 201

SEPARATE THE CRUDE PHENOL STREAM IN A CRUDE PHENOL COLUMN TO PRODUCE A FIRST PHENOL STREAM COMPRISING PRIMARILY PHENOL AND A HEAVY STREAM COMPRISING HEAVY COMPONENTS — 202

CONCURRENTLY PROCESS, IN A HYDROCARBON REMOVAL UNIT, (1) THE FIRST PHENOL STREAM AND (2) AT LEAST A PORTION OF A SECOND WASTE WATER STREAM FROM A BPA PRODUCTION PROCESS UNDER OPERATING CONDITIONS SUFFICIENT TO FORM A PURIFIED PHENOL STREAM COMPRISING PRIMARILY PHENOL AND AN AQUEOUS STREAM COMPRISING WATER, PHENOL, AND/OR BYPRODUCTS FROM THE BPA PRODUCTION PROCESS AND/OR PHENOL PRODUCTION PROCESS — 203

OPTIONALLY COMBINE AT LEAST A PORTION OF THE SECOND WASTE WATER STREAM WITH A FIRST WASTE WATER STREAM FROM A PHENOL PRODUCTION PROCESS TO FORM DEPHENOLATION FEED STREAM COMPRISING PHENOL AND WATER — 204

PROCESS THE DEPHENOLATION FEED STREAM IN A DEPHENOLATION UNIT TO FORM A SECOND PHENOL STREAM COMPRISING PHENOL — 205

RECYCLE THE SECOND PHENOL STREAM TO A PHENOL PRODUCTION PROCESS — 206

PROCESS THE PURIFIED PHENOL STREAM IN A FINISHING COLUMN UNDER FINISHING CONDITIONS SUFFICIENT TO PRODUCE A PHENOL PRODUCT STREAM COMPRISING 99.5 TO 99.9 WT.% PHENOL — 207

*FIG. 2*

SYNERGISTIC USE OF PHENOL PURIFICATION TRAIN IN PHENOL PRODUCTION UNIT FOR PROCESSING PHENOLIC WATER FROM BISPHENOL-A PRODUCTION UNIT

CROSS REFERENCE TO RELATED APPLICATIONS

This application is a National Stage application of PCT/IB2021/059240, filed Oct. 8, 2021, which claims the benefit of priority of U.S. Provisional Patent Application No. 63/090,125, filed Oct. 9, 2020, both of which are hereby incorporated by reference in their entireties herein.

FIELD OF INVENTION

The present invention generally relates to producing to produce bisphenol-A (BPA) and phenol. More specifically, the present invention relates to a system and a method for processing wastewater coming from a BPA production unit, where such wastewater processing is carried out in a purification unit of a phenol production system.

BACKGROUND OF THE INVENTION

Bisphenol-A (BPA) is a precursor for various plastic materials, including polycarbonates, polysulfones, and epoxy resins. These plastic materials are used to manufacture water bottles, food containers, sports equipment, water pipes, etc. Thus, there is a large demand for BPA. Conventionally, BPA is produced by condensation reaction between acetone and phenol. The resulting effluent from the condensation reactor is then dehydrated, crystallized and prilled to produce purified BPA prills.

In the conventional process for producing BPA, a recovery step is implemented to recover and recycle phenol and acetone from the wastewater stream produced at the dehydration step. Generally, the recovery step is conducted using a complex solvent extraction system, thereby resulting in relatively high capital expenditure and high energy consumption for the overall BPA production process.

Overall, while the systems and methods for processing wastewater from the BPA production system exist, the need for improvements in this field persists in light of at least the aforementioned drawbacks of the conventional system and method.

BRIEF SUMMARY OF THE INVENTION

A solution to at least some of the above-mentioned problems associated with systems and methods for processing wastewater from a BPA production unit has been discovered. The solution resides in a method of recovering phenol from the wastewater stream of a BPA production unit including concurrently processing the wastewater stream of the BPA production unit and a phenol stream in a hydrocarbon removing unit of a phenol production unit. This is beneficial for at least simplifying operation due to removing of operation units and reducing the capital expenditure needed for producing BPA as the wastewater stream from BPA production unit can be processed in an existing unit of a phenol production system. Furthermore, at least a portion of the wastewater from the BPA production unit can also be processed in a dephenolation unit in the phenol production unit for recovering phenol, further optimizing the utilization of the processing capacity of the existing phenol production system, and resulting in lower work load for phenolic water purification system and reduced production cost for BPA. Therefore, the method and system of the present invention provide a technical solution to at least the aforementioned problems associated with the conventional system and method for processing wastewater and recovering BPA and/or acetone from the wastewater coming from a BPA production system mentioned above.

Embodiments of the invention include a method of recovering phenol. The method comprises concurrently processing, in a hydrocarbon removal unit, (1) a first phenol stream from a phenol production process and (2) at least a portion of a wastewater stream from a bisphenol-A production process, under operating conditions sufficient to form: (i) a purified phenol stream comprising 95 to 99.9 wt. % phenol and (ii) an aqueous stream comprising water and byproducts of the phenol production process.

Embodiments of the invention include a method of recovering phenol. The method comprises separating an effluent stream coming from a cumene based phenol production process to form (i) a crude phenol stream comprising (a) 60 to 95 wt. % phenol and (b) byproducts from the cumene based phenol production process and (ii) a crude acetone stream comprising 10 to 30 wt. % acetone. The method comprises separating the crude phenol stream in a crude phenol distillation column to produce a first phenol stream. The method comprises concurrently processing, in a hydrocarbon removal unit, (1) the first phenol stream and (2) at least a portion of a wastewater stream from a bisphenol-A production process under operating conditions sufficient to form: (i) a purified phenol stream comprising 95 to 99.9 wt. % phenol and (ii) an aqueous stream comprising water and byproducts of the phenol production process.

Embodiments of the invention include a method of recovering phenol. The method comprises reacting acetone and phenol in an acetone-phenol condensation reaction unit of a bisphenol-A (BPA) production process under reaction conditions sufficient to produce BPA. The method comprises separating an effluent stream from the acetone-phenol condensation reaction unit in a dehydration unit to form (i) a crude bisphenol-A stream comprising 5 to 25 wt. % bisphenol-A and (ii) a wastewater stream from the BPA production process comprising 75 to 95 wt. % water and 2 to 20 wt. % phenol. The method comprises separating an effluent stream from a cumene based phenol production process to form (i) a crude phenol stream comprising (a) 60 to 95 wt. % phenol and (b) byproducts from the cumene based phenol production process and (ii) a crude acetone stream comprising 10 to 30 wt. % acetone. The method comprises separating the crude phenol stream in a crude phenol distillation column to produce a first phenol stream. The method comprises concurrently processing, in a hydrocarbon removal unit, (1) the first phenol stream and (2) at least a portion of the wastewater stream from the BPA production process under operating conditions sufficient to form: (i) a purified phenol stream comprising 95 to 99.9 wt. % phenol and (ii) an aqueous stream comprising water and byproducts of the phenol production process. The method further comprises combining at least a portion of the wastewater stream from the BPA production process with a wastewater stream from the phenol production process to form a dephenolation feed stream. The method further comprises processing the dephenolation feed stream in a dephenolation unit to form a second phenol stream comprising phenol. The method further comprises recycling the second phenol stream to be subjected to the phenol production process.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

4

Figure 1:

FIG. 1 shows a schematic diagram for a system for recovering phenol, according to embodiments of the invention; and FIG. 2 shows a schematic flowchart for a method of recovering phenol, according to embodiments of the invention.

DETAILED DESCRIPTION OF THE INVENTION

Currently, BPA is commonly produced via an acetone-phenol condensation process. Phenol is often produced via a cumene based production process. Both of the processes generate phenol-containing waste streams, which are each individually processed to recover phenol in its own respective recovery unit, thereby requiring capital expenditure and operating costs for two separate phenol recovery processes. The present invention provides a solution to the problem. The solution is premised on a system and a method for recovering phenol that includes processing a wastewater stream from a BPA production process in a hydrocarbon removal unit that is used for phenol production processes, thereby reducing capital expenditure for a separate hydrocarbon removal unit in the BPA production process. Additionally, a portion of the wastewater stream from the BPA production process and a wastewater stream from a phenol production process can be further processed in a dephenolation unit for recovering additional phenol, thereby further optimizing the operating cost for processing wastewater streams from the BPA production process and the phenol production process. These and other non-limiting aspects of the present invention are discussed in further detail in the following sections.

A. System for Recovering Phenol

In embodiments of the invention, the system for recovering phenol comprises a crude phenol distillation column, a hydrocarbon removal unit, and a dephenolation unit. Notably, the system is capable of processing wastewater streams from both a BPA production system and a phenol production system, resulting in reduced capital expenditure and operating costs for producing phenol and BPA, compared to conventional systems. With reference to FIG. 1, a schematic diagram is shown for system 100, which is used for recovering phenol.

According to embodiments of the invention, system 100 comprises crude phenol column 101 configured to separate crude phenol stream 11 to form first phenol stream 12 comprising primarily phenol and heavy stream 13 comprising heavy components. Crude phenol column 101 may include a distillation column. The distillation column may be a vacuum distillation column. In embodiments of the invention, first phenol stream 12 comprises to 99 wt. % phenol. According to embodiments of the invention, crude phenol stream 11 can be obtained from a phenol production system.

In embodiments of the invention, the phenol production system is a cumene based phenol production system comprising an oxidation reaction unit configured to react cumene with air to produce cumene hydroperoxide (CHP), a cumene stripping unit configured to strip cumene from the effluent of the oxidation reaction unit, a cleavage unit configured to decompose the cumene hydroperoxide to produce phenol and acetone under acidic reaction conditions, a neutralization unit configured to neutralize an effluent of the cleavage unit to produce first wastewater stream 14 and a neutralized phenol stream. The phenol production system further comprises an acetone fraction unit configured to separate the neutralized phenol stream to produce crude phenol stream 11 comprising primarily phenol. Crude phenol stream 11 can further comprise cumene, alpha-methylstyrene, heavy components, or combinations thereof.

According to embodiments of the invention, an outlet of crude phenol column 101 is in fluid communication with an inlet of hydrocarbon removal unit 102 such that first phenol stream 12 flows from crude phenol column 101 to hydrocarbon removal unit 102. Hydrocarbon removal unit 102 can be configured to separate first phenol stream 12 and/or at least a portion of second wastewater stream 15, comprising at least some phenol, to produce aqueous stream 16 comprising some phenol, and purified phenol stream 17 comprising phenol. In embodiments of the invention, hydrocarbon removal column 102 includes an extractive distillation column, a hydro-extraction column, a dividing wall column, liquid-liquid contactor, or combinations thereof. Second wastewater stream 15 can be obtained from a BPA production system.

In embodiments of the invention, the BPA production system includes a condensation reaction unit configured to react acetone with phenol to produce BPA, a dehydration unit configured to remove water from an effluent from the condensation reaction unit to produce second wastewater stream 15 comprising phenol and water, and a crude BPA stream comprising BPA. The crude BPA stream may include 5 to 25 wt. % bisphenol-A (BPA). In embodiments of the invention, second wastewater stream 15 further comprises acetone, ketones and/or sodium hydroxide. The BPA production system may further comprise a BPA concentration unit configured to concentrate the crude BPA stream, and an adduct crystallization unit configured to crystalize BPA of an effluent from the concentration unit to produce crystalized BPA and a mother liquor comprising a solvent and water. The BPA production system may further comprise a solvent recovery unit configured to recover the solvent from the solvent recovery unit. In embodiments of the invention, the BPA production system is located near the phenol production system.

According to embodiments of the invention, a top outlet of hydrocarbon removal unit 102 is in fluid communication with the neutralization unit of the phenol production system such that aqueous stream 16 flows from hydrocarbon removal unit 102 to the neutralization unit. A bottom outlet of hydrocarbon removal unit 102 can be in fluid communication with a phenol finishing unit such that purified phenol stream 17 flows to the phenol finishing unit.

According to embodiments of the invention, system 100 further comprises dephenolation unit 103 configured to process first wastewater stream 14 from the phenol production system and/or a portion of second wastewater stream 15 from the BPA production system to produce second phenol stream 18 comprising phenol and acetone. Dephenolation unit 103 may be configured to produce third wastewater stream 19 comprising water and methanol. In embodiments of the invention, dephenolation unit 103 includes a extraction unit, distillation column, decanter, or combinations thereof. Dephenolation unit 103 may be further configured to produce spent solvent stream comprising a solvent including cumene and/or toluene.

According to embodiments of the invention, a first outlet of dephenolation unit 103 is in fluid communication with the phenol production system such that second phenol stream 18 is flowed to the phenol production system. In embodiments of the invention, second phenol stream 18 is recycled into the neutralization unit of the phenol production system. In embodiments of the invention, third wastewater stream 19 can be treated in a biotreatment unit configured to remove phenol using microorganisms before discharging wastewater into the environment.

B. Method of Recovering Phenol

Methods for recovering phenol from wastewater streams of a phenol production system and a BPA production system have been discovered. As shown in FIG. 2, embodiments of the invention include method 200 for recovering phenol. Method 200 may be implemented by system 100, as shown in FIG. 1, and described above.

According to embodiments of the invention, as shown in block 201, method 200 includes processing an effluent stream from a cumene based phenol production process to form (i) crude phenol stream 11 comprising primarily phenol and byproducts from the cumene based phenol production process and (ii) a crude acetone stream comprising acetone. In embodiments of the invention, the effluent stream from a cumene based phenol production process is produced by oxidizing cumene with air to produce cumene hydroperoxide in an oxidation unit, stripping cumene from an effluent stream from the oxidation unit, and decomposing, in a cleavage unit, the cumene hydroperoxide of an effluent of a cumene stripping unit under acidic conditions to produce an effluent comprising phenol and acetone, neutralizing an effluent from the cleavage unit to produce first wastewater stream 14 and the effluent stream from a cumene based phenol production process, which is a neutralized phenol stream comprising phenol and acetone.

In embodiments of the invention, processing at block 201 is conducted in a distillation column, dividing wall column, or combinations thereof. The distillation column can be operated at an overhead boiling range of 60 to 120° C. and a bottom temperature range of 180 to 250° C. The distillation column at block 201 may be operated at an operating pressure of 0.1 to 0.9 bar and all ranges and values there between including ranges of 0.1 to 0.2 bar, 0.2 to 0.3 bar, 0.3 to 0.4 bar, 0.4 to 0.5 bar, 0.5 to 0.6 bar, 0.6 to 0.7 bar, 0.7 to 0.8 bar, and 0.8 to 0.9 bar. In embodiments of the invention, the effluent stream from a cumene based phenol production process comprises 30 to 55 wt. % phenol. Crude phenol stream 11 comprises 60 to 95 wt. % phenol and all ranges and values there between including ranges of 60 to 65 wt. %, 65 to 70 wt. %, 70 to 75 wt. %, 75 to 80 wt. %, 80 to 85 wt. %, 85 to 90 wt. %, and 90 to 95 wt. %. The crude acetone stream produced at block 201 may comprise 10 to 30 wt. % acetone and all ranges and values there between including ranges of 10 to 12 wt. %, 12 to 14 wt. %, 14 to 16 wt. %, 16 to 18 wt. %, 18 to 20 wt. %, 20 to 22 wt. %, 22 to 24 wt. %, 24 to 26 wt. %, 26 to 28 wt. %, and 28 to 30 wt. %.

According to embodiments of the invention, as shown in block 202, method 200 includes separating crude phenol stream 11 in crude phenol column 101 to produce first phenol stream 12 comprising primarily phenol and heavy stream 13 comprising heavy components. In embodiments of the invention, crude phenol column 101 includes a distillation column. The distillation column of crude phenol column 101 is operated at an overhead boiling range of 120 to 180° C. and a bottom temperature range of 180 to 230° C. The distillation column of crude phenol column 101 is operated at an operating pressure of 0.25 to 0.95 bar. First phenol stream 12 can comprise 85 to 99 wt. % phenol and all ranges and values there between including ranges of 85 to 87 wt. %, 87 to 89 wt. %, 89 to 91 wt. %, 91 to 93 wt. %, 93 to 95 wt. %, 95 to 97 wt. %, and 97 to 99 wt. %.

According to embodiments of the invention, as shown in block 203, method 200 includes concurrently processing, in hydrocarbon removal unit 102, (1) first phenol stream 12 and (2) at least a portion of second wastewater stream 15 from a BPA production process under operating conditions sufficient to form purified phenol stream 17 comprising primarily phenol and aqueous stream 16 comprising water, phenol, and/or byproducts from the BPA production process and/or phenol production process. In embodiments of the invention, hydrocarbon removal unit 102 includes a hydro-extraction column configured to perform a liquid-liquid extraction to separate phenol from the byproducts of the phenol production process. The hydro-extraction column can be operated at an overhead boiling range of 90 to 140° C. and a bottom temperature range of 180 to 230° C. At block 203, the hydro-extraction column can be operated at a pressure of 0.4 to 2 bar and all ranges and values there between including ranges of 0.4 to bar, 0.6 to 0.8 bar, 0.8 to 1.0 bar, 1.0 to 1.2 bar, 1.2 to 1.4 bar, 1.4 to 1.6 bar, 1.6 to 1.8 bar, and 1.8 to 2.0 bar. At block 203, the water of second wastewater stream 15 is used as an azeotroping agent in the hydro-extraction column of hydrocarbon removal unit 102 to form azeotrope with the byproducts contained in second wastewater stream 15 and/or first phenol stream 12. In embodiments of the invention, the hydro-extraction column of hydrocarbon removal unit 102 is operated with a solvent comprising water. Second wastewater stream 15 from a BPA production process, in embodiments of the invention, comprises 2 to 20 wt. % phenol and all ranges and values there between including ranges of 2 to 4 wt. %, 4 to 6 wt. %, 6 to 8 wt. %, 8 to 10 wt. %, 10 to 12 wt. %, 12 to 14 wt. %, 14 to 16 wt. %, 16 to 18 wt. %, and 18 to 20 wt. %. Second wastewater stream 15 may further comprise methanol, acetone, acetol, or combinations thereof. Purified phenol stream 17 may include 95 to 99.9 wt. % phenol and all ranges and values there between including 95 to 95.5 wt. %, 95.5 to 96 wt. %, 96 to 96.5 wt. %, 96.5 to 97 wt. %, 97 to 97.5 wt. %, 97.5 to 98 wt. %, 98 to 98.5%, 98.5 to 99 wt. %, 99 to 99.5 wt. %, and 99.5 to 99.9 wt. %. Aqueous stream 16 may comprise 0 to 8 wt. % phenol. In embodiments of the invention, byproducts from the phenol production process include a cumene based phenol production process, such as hydrocarbons, α-methylstyrene, 2-methylbenzofuran, carbonyls, water, acetone, acetophenone, cumylphenol, α-methylstyrene dimers, high boilers, or combinations thereof. Byproducts from a BPA production process include a condensation process between acetone and phenol, may comprise chroman, isopropenyl phenol, isopropenyl phenol dimer, or combinations thereof.

According to embodiments of the invention, as shown in block 204, method 200 includes optionally combining at least a portion of second wastewater stream 15 from a BPA production process with first wastewater stream 14 from a phenol production process to form dephenolation feed stream 21 comprising phenol and water. First wastewater stream 14 may include 2 to 10 wt. % phenol and 85 to 98 wt. % water. First wastewater stream 14 may further comprise acetone, dimethylbenzofuran, cumene, alpha-methylstyrene, or combinations thereof.

According to embodiments of the invention, as shown in block 205, method 200 includes processing dephenolation feed stream 21 in dephenolation unit 103 to form second phenol stream 18 comprising phenol. Alternative to processing dephenolation feed stream 21 at block 205, first wastewater stream 14 and/or a portion of second wastewater stream 15, without being combined, can be separately fed into dephenolation unit 103 and processed in dephenolation unit 103 to produce second phenol stream 18. Second phenol stream 18 may include 0 to 2 wt. % phenol. At block 205, in embodiments of the invention, the processing further produces third wastewater stream 19 comprising water, methanol, acetol, or combinations thereof, and spent solvent stream 22 comprising spent solvent including cumene and/or toluene. Dephenolation unit 103 includes a solvent extraction unit. The solvent extraction unit of dephenolation unit 103 can be operated using a solvent comprising cumene, ethylbenzene, toluene, or combinations thereof. At block 205, dephenolation unit 103 can be operated under operating conditions including a temperature in a range of 20-50° C., and a pressure in a range of 1-8 bar.

According to embodiments of the invention, as shown in block 206, method 200 includes recycling second phenol stream 18 to a phenol production process. In embodiments of the invention, second phenol stream 18 can be recycled to the neutralization unit in a cumene based phenol production system, which is configured to produce first wastewater stream 14 and a neutralized phenol stream comprising phenol and acetone. According to embodiments of the invention, as shown in block 206, method 200 includes separating aqueous stream 16 in a dephenolation unit to recover additional phenol. At block 206, the dephenolation unit may include dephenolation unit 103, and the additional phenol can be recovered in second phenol stream 18. According to embodiments of the invention, as shown in block 207, method 200 further includes processing purified phenol stream 17 in a finishing column under finishing conditions sufficient to produce a phenol product stream. In embodiments of the invention, the finishing column includes a distillation column. The finishing conditions includes an operating pressure for the finishing column in a range of 0.45 to 0.65 bar, in the temperature range of 140-200° C. The phenol product stream may comprise 99.5 to 99.9 wt. % phenol.

As part of the disclosure of the present invention, specific examples are included below. The examples are for illustrative purposes only and are not intended to limit the invention. Those of ordinary skill in the art will readily recognize parameters that can be changed or modified to yield essentially the same results.

Example 1

Simulation of Phenol Recovering System

Simulations of phenol recovering process in the system of the invention and in a conventional phenol recovering system (i.e. separate phenol recovering operation units for phenol production unit and BPA production unit) were conducted on ASPEN platform. The initial conditions for dephenolation unit block 103 includes a temperature of 100° C., and a pressure of 1.5 bar.

The results of the simulation were shown in Table 1, showing the flowrate and compositions for second wastewater stream 15, purified phenol stream 17, and dephenolation stream 21 (referring to FIG. 1) The results indicate that the system of the invention was capable of lowering flowrate of dephenolation stream 21 (inlet of dephenolation unit) compared to the conventional technology, resulting in reduced workload of the dephenolation unit. Additionally, the residual phenol concentration in purified phenol stream 17 is reduced using the system of the invention compared to conventional system, resulting in reduced workload for purifying the phenolic stream 9            10

|  | Conventional | This invention |
|---|---|---|
| Flow rate stream 15 (lb/hr) | 27614 | 29067 |
| Phenol (wt. %) | 0 | 4 |
| Water (wt. %) | 100 | 95 |
| Others (wt. %) | 0 | 1 |
| Flow rate stream 17 (lb/hr) | 68474 | 68474 |
| Phenol (wt. %) | 99 | 99 |
| Flow rate stream 21 | 60101 | 58487 |
| Phenol (wt. %) | 3 | 1 |

Although embodiments of the present invention have been described with reference to blocks of FIG. 2 should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

In the context of the present invention, at least the following 17 embodiments are disclosed. Embodiment 1 is a method of recovering phenol. The method includes concurrently processing, in a hydrocarbon removal unit, (1) a first phenol stream from a phenol production process and (2) at least a portion of a wastewater stream from a bisphenol-A production process under operating conditions sufficient to form: (i) a purified phenol stream containing 95 to 99.9 wt. % phenol and (ii) an aqueous stream containing water and byproducts of the phenol production process. Embodiment 2 is the method of embodiment 1, wherein the first phenol stream contains (a) 85 to 99 wt. % phenol and (b) the byproducts from the phenol production process, and the first phenol stream is produced via a process including separating an effluent stream from a cumene based phenol production process to form (i) a crude phenol stream containing (c) 60 to 95 wt. % phenol and (d) byproducts from the cumene based phenol production process and (ii) a crude acetone stream containing 10 to 30 wt. % acetone. The method further includes separating the crude phenol stream in a crude phenol distillation column to produce the first phenol stream. Embodiment 3 is the method of embodiment 2, wherein the byproducts from the cumene based phenol production process include hydrocarbons, α-methylstyrene, 2-methylbenzofuran, carbonyls, water, acetone, acetophenone, cumylphenol, α-methylstyrene dimers, high boilers, or combinations thereof. Embodiment 4 is the method of any of embodiments 1 to 3, wherein the wastewater stream from the bisphenol-A production process contains 75 to 95 wt. % water and 5 to 20 wt. % phenol. Embodiment 5 is the method of embodiment 4, wherein the wastewater stream from the bisphenol-A production process is produced via separating an effluent stream from an acetone-phenol condensation reaction unit to form (i) a crude bisphenol-A stream containing 5 to 25 wt. % bisphenol-A and (ii) the wastewater stream from the bisphenol-A production process. Embodiment 6 is the method of embodiment 5, wherein the wastewater stream from the bisphenol-A production process further includes acetone, dimethylbenzofuran, cumene, alpha-methylstyrene, or combinations thereof. Embodiment 7 is the method of any of embodiments 4 to 6, further including combining at least a portion of the wastewater stream from the bisphenol A production process with a wastewater stream from a phenol production process to form a dephenolation feed stream. The method further includes processing the dephenolation feed stream in a dephenolation unit to form a second phenol stream containing phenol, and recycling the second phenol stream to a phenol production process. Embodiment 8 is the method of embodiment 7, wherein the wastewater stream from the phenol production process contains 2 to 10 wt. % phenol and 85 to 98 wt. % water. Embodiment 9 is the method of embodiment 8, wherein the wastewater stream from the phenol production process further includes acetone, dimethylbenzofuran, cumene, alpha-methylstyrene, or combinations thereof. Embodiment 10 is the method of any of embodiments 7 to 9, wherein the dephenolation unit includes a solvent extraction unit. Embodiment 11 is the method of embodiment 10, wherein the dephenolation unit is operated using a solvent selected from the group consisting of cumene, ethylbenzene, toluene, and combinations thereof. Embodiment 12 is the method of any of embodiments 1 to 11, wherein the first phenol stream contains 85 to 99 wt. % phenol. Embodiment 13 is the method of any of embodiments 1 to 12, wherein the hydrocarbon removal unit includes a hydro-extraction column configured to perform a liquid-liquid extraction to separate phenol from the byproducts of the phenol production process. Embodiment 14 is the method of embodiment 13, wherein the hydro-extraction column is operated to provide an extraction temperature of 100 to 250° C. and an extraction pressure of 0.4 to 2 bar. Embodiment 15 is the method of either of embodiments 13 or 14, wherein the water of the wastewater stream from the bisphenol-A production process is used as an azeotroping agent in the hydro-extraction column configured to form azeotrope with the byproducts of the phenol production process. Embodiment 16 is the method of any of embodiments 1 to 15, wherein the aqueous stream from the hydrocarbon removal unit further contains phenol, and the method further includes separating the aqueous stream in a dephenolation unit to recover additional phenol. Embodiment 17 is the method of any of embodiments 1 to 16, further including processing the purified phenol stream in a finishing column under finishing conditions sufficient to produce a phenol product stream containing 99.5 to 99.9 wt. % phenol.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of recovering phenol, the method comprising:

concurrently processing, in a hydrocarbon removal unit, (1) a first phenol stream from a phenol production process and (2) at least a portion of a wastewater stream from a bisphenol-A production process under operating conditions sufficient to form: (i) a purified phenol stream comprising 95 to 99.9 wt. % phenol and (ii) an aqueous stream comprising water and byproducts of the phenol production process, wherein the hydrocarbon removal unit includes a hydro-extraction column configured to perform a liquid-liquid extraction to separate phenol from the byproducts of the phenol production process, wherein the hydro-extraction column is operated to provide an extraction temperature of 100 to 250° C. and an extraction pressure of 0.4 to 2 bar.

2. The method of claim 1, wherein the first phenol stream comprises (a) 85 to 99 wt. % phenol and (b) the byproducts from the phenol production process, and the first phenol stream is produced via a process comprising:

separating an effluent stream from a cumene based phenol production process to form (i) a crude phenol stream comprising (c) 60 to 95 wt. % phenol and (d) byproducts from the cumene based phenol production process and (ii) a crude acetone stream comprising 10 to 30 wt. % acetone; and separating the crude phenol stream in a crude phenol distillation column to produce the first phenol stream.

3. The method of claim 2, wherein the byproducts from the cumene based phenol production process comprise hydrocarbons, α-methylstyrene, 2-methylbenzofuran, carbonyls, water, acetone, acetophenone, cumylphenol, α-methylstyrene dimers, high boilers, or combinations thereof.

4. The method of claim 1, wherein the wastewater stream from the bisphenol-A production process comprises 75 to 95 wt. % water and 5 to 20 wt. % phenol.

5. The method of claim 4, wherein the wastewater stream from the bisphenol-A production process is produced via separating an effluent stream from an acetone-phenol condensation reaction unit to form (i) a crude bisphenol-A stream comprising 5 to 25 wt. % bisphenol-A and (ii) the wastewater stream from the bisphenol-A production process.

6. The method of claim 5, wherein the wastewater stream from the bisphenol-A production process further comprises acetone, dimethylbenzofuran, cumene, alpha-methylstyrene, or combinations thereof.

7. The method of claim 4, further comprising:

combining at least a portion of the wastewater stream from the bisphenol A production process with a wastewater stream from a phenol production process to form a dephenolation feed stream;

processing the dephenolation feed stream in a dephenolation unit to form a second phenol stream comprising phenol; and recycling the second phenol stream to a phenol production process.

8. The method of claim 7, wherein the wastewater stream from the phenol production process comprises 2 to 10 wt. % phenol and 85 to 98 wt. % water.

9. The method of claim 8, wherein the wastewater stream from the phenol production process further comprises acetone, dimethylbenzofuran, cumene, alpha-methylstyrene, or combinations thereof.

10. The method of claim 7, wherein the dephenolation unit includes a solvent extraction unit.

11. The method of claim 10, wherein the dephenolation unit is operated using a solvent selected from the group consisting of cumene, ethylbenzene, toluene, and combinations thereof.

12. The method of claim 1, wherein the first phenol stream comprises 85 to 99 wt. % phenol.

13. The method of claim 1, wherein the water of the wastewater stream from the bisphenol-A production process is used as an azeotroping agent in the hydro-extraction column configured to form azeotrope with the byproducts of the phenol production process.

14. The method of claim 1, wherein the aqueous stream from the hydrocarbon removal unit further comprises phenol, and the method further comprises separating the aqueous stream in a dephenolation unit to recover additional phenol.

15. The method of claim 1, further comprising:

processing the purified phenol stream in a finishing column under finishing conditions sufficient to produce a phenol product stream comprising 99.5 to 99.9 wt. % phenol.

* * * * *